US009457037B2

(12) United States Patent
Virmani et al.

(10) Patent No.: US 9,457,037 B2
(45) Date of Patent: Oct. 4, 2016

(54) COMBINATION COMPOSITION, COMPRISING AS ACTIVE INGREDIENTS L-CARNITINE OR PROPIONYL L-CARNITINE, FOR THE PREVENTION OR TREATMENT OF CHRONIC VENOUS INSUFFICIENCY

(71) Applicant: SIGMA-TAU INDUSTRIE FARMACEUTICHE RIUNITE S.P.A., Rome (IT)

(72) Inventors: Mohamed Ashraf Virmani, Rome (IT); Aleardo Koverech, Rome (IT)

(73) Assignee: SIGMA-TAU INDUSTRIE FARMACEUTICHE RIUNITE S.P.A., Rome (IT)

( * ) Notice: Subject to any disclaimer, the term of this patent is extended or adjusted under 35 U.S.C. 154(b) by 611 days.

(21) Appl. No.: 14/031,555

(22) Filed: Sep. 19, 2013

(65) Prior Publication Data

US 2014/0018310 A1 Jan. 16, 2014

Related U.S. Application Data

(62) Division of application No. 13/022,102, filed on Feb. 7, 2011, now abandoned.

(60) Provisional application No. 61/322,532, filed on Apr. 9, 2010.

(51) Int. Cl.

| | |
|---|---|
| *A61K 38/48* | (2006.01) |
| *A61K 31/205* | (2006.01) |
| *A61K 31/221* | (2006.01) |
| *A61K 45/06* | (2006.01) |
| *A61K 31/7048* | (2006.01) |

(52) U.S. Cl.

CPC ......... *A61K 31/7048* (2013.01); *A61K 31/205* (2013.01); *A61K 31/221* (2013.01); *A61K 45/06* (2013.01)

(58) Field of Classification Search

CPC . A61K 2300/00; A61K 31/221; A61K 45/06

See application file for complete search history.

(56) References Cited

U.S. PATENT DOCUMENTS

| | | | |
|---|---|---|---|
| 4,415,589 | A | 11/1983 | Cavazza |
| 5,849,786 | A | 12/1998 | Bidel et al. |
| 2004/0053860 | A1 | 3/2004 | Buchholz et al. |

FOREIGN PATENT DOCUMENTS

| | | | |
|---|---|---|---|
| WO | 00/28986 | A1 | 5/2000 |
| WO | 03/066573 | | 8/2003 |
| WO | 2006/089317 | A1 | 8/2006 |
| WO | 2009/031878 | A1 | 3/2009 |

OTHER PUBLICATIONS

International Search Report for International Application No. PCT/IB2011/000200, dated Apr. 11, 2011.

*Primary Examiner* — Sharmila G. Landau
*Assistant Examiner* — Sheridan Macauley
(74) *Attorney, Agent, or Firm* — Lucas & Mercanti, LLP

(57) ABSTRACT

A combination composition comprising as active ingredients L-carnitine or propionyl L-carnitine, troxerutine, diosmine and hesperidine, useful for the prevention and/or treatment of chronic venous diseases.

16 Claims, No Drawings

COMBINATION COMPOSITION, COMPRISING AS ACTIVE INGREDIENTS L-CARNITINE OR PROPIONYL L-CARNITINE, FOR THE PREVENTION OR TREATMENT OF CHRONIC VENOUS INSUFFICIENCY

RELATED APPLICATIONS

This application is a divisional application of U.S. Ser. No. 13/022,102 filed on Feb. 7, 2011 which claims priority to and benefit of U.S. Provisional Application No. 61/322,532 filed Apr. 9, 2010, the contents of which are herein incorporated by reference in their entirety.

FIELD OF THE INVENTION

The present invention relates to a combination composition comprising as active ingredients L-carnitine or a derivative thereof, or a salt thereof, troxerutine, diosmine and hesperidine, useful for the prevention and/or treatment of chronic venous insufficiency (CVI).

BACKGROUND OF THE INVENTION

In humans, arteries bring oxygen-rich blood from the heart to the rest of the body and veins return oxygen-poor blood back to the heart. When human leg veins cannot pump enough blood back to heart, there is the onset of chronic venous insufficiency (CVI). CVI is also sometimes called chronic venous disease, or CVD.

Humans have three kinds of veins: superficial veins, which lie close to the skin, deep veins, which lie in groups of muscles, and perforating veins, which connect the superficial to the deep veins. Deep veins lead to the vena cava, human body's largest vein, which runs directly to the heart.

When humans are in the upright position, the blood in their leg veins must go against gravity to return to our heart. To accomplish this, leg muscles squeeze the deep veins of their legs and feet to help move blood back to our heart. One-way flaps, called valves, in the veins keep blood flowing in the right direction. When the leg muscles relax, the valves inside the veins close. This prevents blood from flowing in reverse, back down the legs. The entire process of sending blood back to the heart is called the venous pump.

When humans walk and the leg muscles squeeze, the venous pump works well. But when patient sit or stand, especially for a long time, the blood in the leg veins can pool and increase the venous blood pressure. Deep veins and perforating veins are usually able to withstand short periods of increased pressures. However, sitting or standing for a long time can stretch vein walls because they are flexible. Over time, in susceptible individuals, this can weaken the walls of the veins and damage the vein valves, causing CVI.

During CVI ankles may swell and calves may feel tight. The legs may also feel heavy, tired, restless, or achy. Patient may feel pain while walking or shortly after stopping.

CVI may be associated with varicose veins. Varicose veins are swollen veins that we can see through the skin. They often look blue, bulging, and twisted. Large varicose veins can lead to skin changes like rashes, redness, and sores.

CVI can also cause problems with leg swelling because of the pressure of the blood pooling in the veins. The lymphatic system may also produce fluid, called lymph, to compensate for CVI. Human leg tissues may then absorb some of this fluid, which can increase the tendency for the legs to swell. In severe cases, CVI and the leg swelling can cause ulcers to form on the lower parts of the leg.

Over the long-term, blood pressure that is higher than normal inside the leg veins causes CVI. Other causes of CVI include deep vein thrombosis (DVT) and phlebitis, both of which cause elevated pressure in our veins by obstructing the free flow of blood through the veins.

DVT occurs when a blood clot (properly called a thrombus) blocks blood from flowing toward the heart, out of a deep or perforating vein. The blood trying to pass through the blocked veins can increase the blood pressure in the vein, which, in turn, overloads our valves. Vein valves that do not work properly are called incompetent because they stretch and no longer work efficiently, and incompetent valves contribute to CVI. DVT is a potentially serious condition that causes leg swelling and requires immediate medical attention because sometimes the blood clots in the veins can break off and travel to the lungs. This condition is called a pulmonary embolus.

Phlebitis occurs when a superficial or deep vein becomes swollen and inflamed. This inflammation causes a blood clot to form, which can also lead to DVT.

Factors that can increase the risk for CVI include a family history of varicose veins, being overweight, being pregnant, not exercising enough, smoking, and standing or sitting for long periods of time. Although CVI can affect anyone, age and sex can also be factors that may increase the tendency to develop CVI; women older than 50 most often get CVI.

For mild cases of CVI, physician may recommend compression stockings. Compression stockings are elastic stockings that squeeze the veins and stop excess blood from flowing backward. In this way, compression stockings can often also help heal skin sores and prevent them from returning. Patient may need to wear compression stockings daily for the rest of the life.

More serious cases of CVI may be treated with injections, called sclerotherapy, or with surgical procedures. Fewer than 10 percent of patient with CVI require surgery to correct the problem. Surgical treatments include ablation, vein stripping, bypass surgery, valve repair, and angioplasty or stenting of a vein.

The flavonoids, troxerutine, diosmine and hesperidine, also referred to as rutins oxerutins or rutosides, are well known for their antioxidant properties, in addition they also display other properties that impact upon the circulatory system i.e. blood and microvascular endothelial cells (G.I.O.T. 2009; 35:23-33).

Many epidemiological studies suggest that these flavonoids are associated with improvement of circulation and a general reduced risk of cardiovascular diseases. The mechanisms underlying these protective actions include antithrombotic, anti-ischemic, anti-oxidant, and vasorelaxant properties. In particular these flavonoids have actions that improve circulation by vasodilatation, decreasing platelets clotting and preventing low-density lipoproteins (LDLs) from oxidizing (Journal of Agricultural and Food Chemistry 2008 56 (15), pp 6185-6205).

These flavonoids also demonstrate strong anti-inflammatory properties that are thought to be the result of the inhibition of the synthesis and biological activities of different pro-inflammatory mediators, mainly the arachidonic acid derivatives, prostaglandins E2, F2, and thromboxane A2. These processes improve venous tone and lymphatic drainage, and reduce capillary hyperpermeability by protecting the microcirculation from inflammatory processes.

This effect has been shown also in clinical studies. The study of Belcaro et al (Angiology, 59; 5S) showed that these flavonoids were effective in the control and treatment of oedema and increased capillary filtration in venous hypertension and diabetic microangiopathy.

Another study by Belcaro et al. (Angiology, Mar. 1, 2008; 59 (1) suppl. 7S-13S) also looked at the use of these flavonoids in the treatment of chronic venous disease and signs and symptoms of chronic venous insufficiency (CVI), varicose veins, and deep venous disease.

In Rev Fr Gynecol Obstet. 1991 Feb. 25; 86 (2 Pt 2): 209-12, is reported that troxerutine in women (half in the context of premenstrual syndrome and half in pregnant) was useful for the treatment of vulval varicosities and venous insufficiency of the lower limbs.

In Br. J. Surg. 2000, 87; 868-872, it is reported that diosmine has anti-inflammatory actions that play a role in protecting the blood vessels and contributes to the maintenance of good circulation of the blood and maintains the venous tone.

In Farmaco, 40 (11); 709-712, it is reported that hesperidine has an antioxidant action and together with troxerutine and diosmine promotes healthy vessel functions.

In U.S. Pat. No. 4,255,449 it is reported that L-carnitine is useful for increasing the HDL cholesterol and for treating diseases liked to high cholesterol level.

In WO04091602 9 it is reported that L-carnitine is useful the treatment of cardiovascular diseases.

In U.S. Pat. No. 5,811,457 it is reported that propionyl L-carnitine is useful the treatment of chronic arteriosclerosis obliterans In WO 2007045639 it is reported that propionyl L-carnitine is useful the treatment of left ventricular hypertrophy in dialysed patients.

In U.S. Pat. No. 4,343,816 it is reported that propionyl L-carnitine is useful the treatment of peripheral vascular diseases.

Furthermore, while there are other publications available in which is shown that the compounds of the invention are useful for the treatment of diseases of the veins, none of them mention nor suggest about the unexpected synergistic effect shown by the composition of the invention.

DESCRIPTION OF THE INVENTION

It has now been found that a combination composition comprising as active ingredients L-carnitine or a derivative thereof (e.g. propionyl L-carnitine) or a salt thereof, troxerutine, diosmine and hesperidine, is endowed with a surprisingly synergistic effect for the prevention and/or treatment of diseases of the veins selected from Chronic venous insufficiency (CVI) and chronic venous disease (CVD) or their complications.

An example of complications or diseases of the veins (due to CVI or CVD) are reported in the following: swelling and inflammation of veins in the rectum, anus and vulva; venous hypertension; increased permeability; oedema; capillary damage; skin changes; venous leg ulcers; swelling ankles; heavy legs; varicose veins; swelling leg; ulcers; vein thrombosis; phlebitis; thrombo-phlebitis; pulmonary embolus; hemorrhoids.

It is therefore one object of the present invention a combination composition comprising as active ingredients L-carnitine or a salt thereof, troxerutine, diosmine and hesperidine.

It is a further object of the present invention a combination composition comprising as active ingredients propionyl L-carnitine or a salt thereof, troxerutine, diosmine and hesperidine.

The compositions mentioned above may further comprise other active ingredients useful for treating diseases of the vein.

It is a further object of the present invention a composition comprising:

(a) L-carnitine or propionyl L-carnitine, in a dose of from 10 to 3000 mg, preferred doses is of from 50 mg to 400 mg, the most preferred dose is 136 mg.

(b) troxerutine, in a dose of from 900 mg to 50 mg, preferred doses is of from 400 mg to 200 mg, the most preferred dose is 300 mg;

(c) diosmine, in a dose of from 900 mg to 50 mg, preferred doses is of from 400 mg to 200 mg, the most preferred dose is 300 mg; and (d) hesperidine in a dose of from 10 mg to 500 mg, preferred doses is of from 50 mg to 200 mg, the most preferred dose is 100 mg.

It is a further object of the present invention the composition mentioned above, for use as anti-chronic venous insufficiency and complications thereof.

It is a further object of the present invention the composition mentioned above, for use as anti-chronic venous disease and complications thereof.

It is a further object of the present invention the use of the composition mentioned above, for preparing a medicament for the prevention or treatment of chronic venous insufficiency, chronic venous disease and complications thereof, in which said complications are selected from the group comprising: swelling and inflammation of veins in the rectum, anus and vulva; venous hypertension; increased permeability; oedema; capillary damage; skin changes; venous leg ulcers; swelling ankles; heavy legs; varicose veins; swelling leg; ulcers; vein thrombosis; phlebitis; thrombo-phlebitis; pulmonary embolus or hemorrhoids.

It is a further object of the present invention the use of the composition mentioned above, for preparing a dietary supplement for the prevention or treatment of chronic venous insufficiency, chronic venous disease and complications thereof.

The composition of the invention may further comprise co-enzymes, mineral substances, antioxidants, vitamins, anticloting agents and agents useful for treating diseases of the veins.

What is meant by salt of L-carnitine is any salt of the latter with an acid that does not give rise to toxic or side effects.

Non-limiting examples of such salts are: chloride, bromide, orotate, aspartate, acid aspartate, acid citrate, magnesium citrate, phosphate, acid phosphate, fumarate and acid fumarate, magnesium fumarate, lactate, maleate and acid maleate, oxalate, acid oxalate, pamoate, acid pamoate, sulphate, acid sulphate, glucose phosphate, tartrate and acid tartrate, glycerophosphate, mucate, magnesium tartrate, 2-amino-ethanesulphonate, magnesium 2-amino-ethanesulphonate, methanesulphonate, choline tartrate, trichloroacetate, and trifluoroacetate.

A list of FDA-approved pharmaceutically acceptable salts is given in the publication Int. J. of Pharm. 33 (1986), 201-217.

L-carnitine, propionyl L-carnitine, troxerutine, diosmine and hesperidine according to the present invention can be administrated in a "co-ordinated manner". What is meant by "co-ordinated manner" of the aforesaid compounds is, indifferently, either the co-administration, i.e. the substantially concomitant or sequential supplementation of L-carnitine or propionyl L-carnitine and at least one troxerutine, diosmine, hesperidine, or the administration of a composition comprising the aforesaid active ingredients in combination and in a mixture optionally further comprising one or more excipients or diluents pharmaceutically acceptable.

The composition of the present invention can be administered orally, parenterally, intravenously, topically and/or transdermally, in any suitable form. The oral administration is preferred.

An example of form of administration is in a liquid, semi-liquid or solid form in sachets, pills, vials, ointment, gel or liposome.

L-carnitine and propionyl L-carnitine are known compounds and their preparation process is described in U.S. Pat. No. 4,254,053.

Troxerutine, diosmine and hesperidine are widely sold on the market and their CAS-No. are: 7085-55-4; 520-27-4 and 520-26-3 respectively.

The pharmaceutical composition according to the present invention is composed of active ingredients which are familiar to operators in the medical field and already in use.

Their procurement therefore is very easy, inasmuch as these are products which have been on the market now for a long time and are of a grade suitable for human administration.

For any compound, the therapeutically effective dose can be estimated initially either in cell culture assays or in animal models, usually mice or rats.

The animal model may also be used to determine the appropriate concentration range and route of administration. Such information can then be used to determine useful doses and routes for administration in humans.

The precise effective dose for a human subject will depend upon the severity of the disease state, general health of the subject, age, weight, and gender of the subject, diet, time and frequency of administration, drug combination(s), reaction sensitivities, and tolerance/response to therapy. This amount can be determined by routine experimentation and is within the judgement of the clinician.

The following non limiting examples further illustrate the invention.

EXAMPLE 1

Reduction of the Swelling of the Recto-Anus, in Croton Oil-Induced Hemorrhoid Model in Rats Male SD rats (6 weeks old, approximately 140 g) were purchased from Harlan Sprague Dawley and allowed to acclimate for 1 week. The rats were maintained in a pathogen-free facility in accordance with the National Research Council of Laboratory Animal care and use guidelines. Each experiment was preformed with age-matched rats 7-8 weeks old. The croton oil-induced hemorrhoid model in rats was performed according to the method published by Nishiki (Nishiki et al. (1988) Folia Pharmacology Japan 92:215-225; Nishiki et al. (1988) Folia Pharmacol. Japan 92:227-240). Briefly, a cotton swab with a diameter of 4 mm soaked with 0.16 mL of inducer (deionized water:pyridine:ethyl ether:6% croton oil/ethyl ether (1:4:5:10) was applied to the rat's anus for 12 seconds. The final concentration of croton oil was 3%. The edema developed linearly until 7-8 hours after application and the severity of the edema was sustained for more than 24 hours. Twenty-four hours later, recto-anus tissue (approx. 10 mm long) was isolated after the rats were euthanized. The weights of rat body and recto-anus were measured. The recto-anus coefficient (RAC) was calculated using the formula: weight of recto-anus (mg)/body weight (g).

The compounds of the invention were administered orally suspended in saline (1 mL) once per day for five days. Last treatment with the compounds of the invention was made the day of induction of oedema with croton oil.

The compounds of the invention were administered alone or in combination at the following doses: 20 mg/kg propionyl L-carnitine or L-carnitine; 30 mg/kg troxerutine, diosmine or hesperidine.

Twenty-four hours after hemorrhoid induction with croton oil the RAC of rats was determined.

The results obtained are reported in the following Table 1.

TABLE 1 n = 5 rats per group; degrees of freedom = 8.

| | | RAC | SE | P< |
|---|---|---|---|---|
| 1 | Vehicle alone | 1.28 | 0.14 | — |
| 2 | No treatment | 0.97 | 0.11 | −NS vs 1 |
| 3 | L-carnitine + Troxerutine + diosmine + hesperidine. 20 mg/kg + 30 mg/kg + 30 mg/kg + 30 mg/kg. | 1.33 | 0.12 | −NS vs 1 |
| 4 | Propionyl L-carnitine + Troxerutine + diosmine + hesperidine. 20 mg/kg + 30 mg/kg + 30 mg/kg + 30 mg/kg. | 1.31 | 0.11 | −NS vs 1 |
| 5 | crotonoil (3%) | 253 | 0.18 | 0.001 vs 1 |
| 6 | L-carnitine + Troxerutine + diosmine + hesperidine + croton oil. | 1.34 | 0.09 | −NS vs 1<br>−NS vs 3<br>−NS vs 4<br>−0.001 vs 5<br>−0.001 vs 8<br>−0.001 vs 9<br>−0.001 vs 10<br>−0.001 vs 11<br>−0.001 vs 12<br>−0.05 vs 21 |
| 7 | Propionyl L-carnitine + Troxerutine + diosmine + hesperidine + croton oil. | 1.32 | 0.11 | −NS vs 1<br>−NS vs 3<br>−NS vs 4<br>−0.001 vs 5<br>−0.001 vs 8<br>−0.001 vs 9<br>−0.001 vs 10<br>−0.001 vs 11<br>−0.001 vs 12<br>−0.05 vs 21 |
| 8 | Troxerutine + croton oil | 2.11 | 0.19 | 0.05 vs 1 |
| 9 | Diosmine + croton oil | 2.02 | 0.18 | 0.05 vs 1 |
| 10 | Hesperidine + croton oil | 2.07 | 0.20 | 0.05 vs 1 |
| 11 | L-carnitine + croton oil | 1.99 | 0.18 | 0.05 vs 1 |
| 12 | Propionyl L-carnitine + croton oil | 1.96 | 0.16 | 0.05 vs 1 |
| 13 | Troxerutine + diosmine + croton oil | 2.00 | 0.20 | 0.05 vs 1 |
| 14 | Troxerutine + hesperidine + croton oil | 1.99 | 0.18 | 0.05 vs 1 |
| 15 | troxerutine + L-carnitine + croton oil | 1.91 | 0.17 | 0.05 vs 1 |
| 16 | Troxerutine + propionyl 1-carnitine + croton oil | 1.89 | 0.17 | 0.05 vs 1 |
| 17 | Diosmine + hesperidine + croton oil | 2.01 | 0.21 | 0.05 vs 1 |
| 18 | Diosmine + L-carnitine + croton oil | 1.87 | 0.15 | 0.05 vs 1 |
| 19 | Diosmine + propionyl L-carnitine | 1.83 | 0.13 | 0.05 vs 1 |
| 20 | Hesperidine + L-carnitine + croton oil | 1.84 | 0.14 | 0.05 vs 1 |
| 20 | Hesperidine + propionyl L-carnitine + croton oil | 1.84 | 0.13 | 0.05 vs 1 |
| 21 | Troxerutine + hesperidine + diosmine + croton oil | 1.65 | 0.14 | NS vs 1<br>−0.05 vs 5 |

The results reported in Table 1 show that using the compositions of the invention results statistically significant more active (respect to the use of single component) were obtained.

In fact, the results reported in Table 1 show that the compositions of the invention completely inhibited the swelling of the recto-anus induced by croton oil.

EXAMPLE 2

Relaxant Effect on Aortic Rings of the Compounds Tested

The objective of this study was to investigate the vasoarelaxation effects of the compositions of the invention using isolated aorta from spontaneously hypertensive rats.

Materials and Methods

The compounds tested were used at a concentration expressed as final concentration in the organ chamber.

Animals

Male spontaneously hypertensive rats (SHR) 10-12 weeks old, weighing 250-300 g, were housed at 24±2° C. with 60±20% relative humidity, on a 12-h light-dark cycle. Rats were given free access to a diet of standard food and water. All experiments were performed according to the guidelines for the ethical treatment of animals of the European Union. The rats were killed by cervical dislocation and the aortae were rapidly dissected.

Aortic Ring Preparation

The descending thoracic aorta was placed in a modified Krebs-Henseleit solution (PSS) containing (mM): NaCl 118, KCl 4.75, $NaHCO_3$ 25, $MgSO_4$ 1.2, $CaCl_2$ 1.8, $KH_2PO_4$ 1.2 and glucose 11.

After excess fat and connective tissue were removed, the aortae were cut into 2-3-mm rings. Aortic rings were mounted under a basal tension of 2 g in 20 mL organ baths containing PSS and attached to an isometric transducer (Harvard UF-1); the signal was recorded by a Powerlab data acquisition system (AD-Instruments). The tissue bath was maintained at 37° C. and bubbled with a 95% $O_2$ and 5% $CO_2$ gas mixture.

Relaxant Effect of the Compounds Tested.

The relaxant effect of compounds tested was assessed by adding the compound to aortic rings precontracted by phenylephrine (1 micromolar).

After the aortae were contracted with phenylephrine and when the contractile response was reached, the test compound was added to the bath. All the results were expressed as a percentage of the maximal contraction of phenylephrine-induced responses.

Statistical Analysis

Results are expressed as percentages from the initial precontraction level.

The significance was calculated on the actual contraction values means±SE (n=8 aorta preparations per group). Eight preparations were studied from a single aorta. The Student t-test was used as the comparison test for statistical analysis.

$p<0.05$ Values were considered to represent a significant difference.

The results obtained are reported in the following Table 2.

TABLE 2

| | TREATMENT | % RELAXATION | P< |
|---|---|---|---|
| 1 | Saline | 0 | — |
| 2 | L-carnitine + troxerutine + hesperidine + diosmine (100 micro-molar + 100 micro-molar + 100 micro-molar + 100 micro-molar). | 52 | −0.001 vs 1<br>−0.01 vs 4<br>−0.01 vs 5<br>−0.01 vs 6<br>−0.05 vs 7<br>−0.05 vs 8<br>−0.05 vs 18 |
| 3 | Propionyl L-carnitine + troxerutine + hesperidine + diosmine. (100 micro-molar + 100 micro-molar + 100 micro-molar + 100 micro-molar). | 53 | −0.001 vs 1<br>−0.01 vs 4<br>−0.01 vs 5<br>−0.01 vs 6<br>−0.05 vs 7<br>−0.05 vs 8<br>−0.05 vs 18 |
| 4 | Troxerutine (100 micro-molar). | 10 | −0.05 vs 1 |
| 5 | Diosmine (100 micro-molar). | 10 | 0.05 vs 1 |
| 6 | Hesperidine (100 micro-molar). | 9 | 0.05 vs 1 |
| 7 | L-carnitine (100 micro-molar). | 25 | 0.01 vs 1 |
| 8 | Propionyl L-carnitine (100 micro-molar). | 28 | 0.01 vs 1 |
| 9 | Troxerutine + diosmine | 12 | 0.05 vs 1 |
| 10 | Troxerutine + hesperidine | 13 | 0.05 vs 1 |
| 11 | Troxerutine + L-carnitine | 27 | 0.01 vs 1 |
| 12 | Troxerutine + propionyl L-carnitine | 29 | 0.01 vs 1 |
| 13 | Diosmine + hesperidine | 14 | 0.05 vs 1 |
| 14 | Diosmine + L-carnitine | 26 | 0.01 vs 1 |
| 15 | Diosmine + propionyl L-carnitine | 28 | 0.01 vs 1 |
| 16 | Hesperidine + L-carnitine | 26 | 0.01 vs 1 |
| 17 | Hesperidine + propionyl L-carnitine | 29 | 0.01 vs 1 |
| 18 | Troxerutine + hesperidine + diosmine | 35 | 0.001 vs 1 |

The results reported in Table 2 show that the addition of compositions of the invention to aortic rings precontracted with phenylephrine elicited endothelium-dependent relaxation which was statistically significant more active respect to the single components.

In the following are reported some non limiting examples of the compositions of the invention.

Composition 1

| | |
|---|---|
| L-Carnitine tartrate | 200 mg |
| Equivalent to L-carnitine | 136 mg |
| Troxerutine NEC ® | 700 mg |
| Comprising Troxerutina | 300 mg |
| Diosmine | 300 mg |
| Hesperidine 98% | 100 mg |
| Equivalent to Hesperidine | 98 mg. |

Composition 2

| | |
|---|---|
| Propionyl L-Carnitine tartrate | 250 mg |
| Equivalent to propionyl L-carnitine | 136 mg |
| Troxerutine NEC ® | 700 mg |
| Comprising Troxerutina | 300 mg |
| Diosmine | 300 mg |
| Hesperidine 98% | 100 mg |
| Equivalent to Hesperidine | 98 mg. |

Composition 3

| | |
|---|---|
| L-Carnitine fumarate | 200 mg |
| Equivalent to L-carnitine | 136 mg |
| Troxerutine NEC ® | 700 mg |
| Comprising Troxerutina | 300 mg |
| Diosmine | 300 mg |
| Hesperidine 98% | 100 mg |
| Equivalent to Hesperidine | 98 mg. |

Composition 4

| | |
|---|---|
| Propionyl L-Carnitine fumarate | 250 mg |
| Equivalent to propionyl L-carnitine | 136 mg |
| Troxerutine NEC ® | 700 mg |
| Comprising Troxerutina | 300 mg |
| Diosmine | 300 mg |
| Hesperidine 98% | 100 mg |
| Equivalent to Hesperidine | 98 mg. |

The invention claimed is:

1. A method for treating diseases of the veins, wherein the diseases of the veins are selected from the group consisting of chronic venous insufficiency and chronic venous disease, the method comprising: administering to a patient in need thereof an effective amount of a combination composition comprising L-carnitine or propionyl L-carnitine or a salt thereof, troxerutine, diosmine and hesperidine.

2. The method of claim 1, wherein the composition further comprises one or more pharmaceutically acceptable excipient.

3. The method of claim 1, wherein the composition comprises:

from 10 to 3000 mg of L-carnitine or propionyl L-carnitine, from 50 to 900 mg of troxerutine, from 50 to 900 mg of diosmine, and from 10 to 500 mg of hesperidine.

4. The method of claim 3, wherein the L-carnitine or the propionyl L-carnitine is in a dose of from 50 mg to 400 mg.

5. The method of claim 3, wherein the L-carnitine or propionyl L-carnitine is in a dose of 136 mg.

6. The method of claim 3, wherein the troxerutine is in a dose of from 200 mg to 400 mg.

7. The method of claim 3, wherein the troxerutine is in a dose of 300 mg.

8. The method of claim 3, wherein the diosmine is in a dose of from 200 mg to 400 mg.

9. The method of claim 3, wherein the diosmine is in a dose of 300 mg.

10. The method of claim 3, wherein the hesperidine is in a dose of from 50 mg to 200 mg.

11. The method of claim 3, wherein the hesperidine is in a dose of 100 mg.

12. The method of claim 1, wherein the composition further comprises co-enzymes, mineral substances, antioxidants, vitamins and anticlotting agents.

13. The method of claim 1, wherein the treatment is for complications of chronic venous insufficiency or chronic venous disease, wherein said complications are selected from the group consisting of: swelling and inflammation of veins in the rectum, anus and vulva; venous hypertension; increased permeability; oedema; capillary damage; skin changes; venous leg ulcers; swelling ankles; heavy legs; varicose veins; swelling leg; ulcers; vein thrombosis; phlebitis; thrombo-phlebitis; pulmonary embolus and hemorrhoids.

14. The method of claim 1, wherein the salt of L-carnitine or propionyl L-carnitine is selected from the group consisting of: chloride, bromide, orotate, aspartate, acid aspartate, acid citrate, magnesium citrate, phosphate, acid phosphate, fumarate and acid fumarate, magnesium fumarate, lactate, maleate and acid maleate, oxalate, acid oxalate, pamoate, acid pamoate, sulphate, acid sulphate, glucose phosphate, tartrate and acid tartrate, glycerophosphate, mucate, magnesium tartrate, 2-amino-ethanesulphonate, magnesium 2-amino-ethane-sulphonate, methanesulphonate, choline tartrate, trichloroacetate and trifluoroacetate.

15. The method of claim 1, wherein the combination composition is for oral, parenteral, intravenous, topical and/or transdermal administration.

16. The method of claim 15, wherein the combination composition is for oral administration.

* * * * *